United States Patent [19]
Kirkham et al.

[11] Patent Number: 5,615,678
[45] Date of Patent: Apr. 1, 1997

[54] INTEGRAL AUTO-SELECTING YOKE/TRANSDUCER CONNECTOR FOR ULTRASOUND TRANSDUCER PROBE

[75] Inventors: Thomas R. Kirkham, Dousman; Kirsten N. Laconte, Waukesha; Michael L. Hall, Pewaukee; Jonathan E. Snyder, Whitefish Bay, all of Wis.; Edward S. Wallace, Tempe, Ariz.; William H. Phillips, Jr., Issaquah, Wash.; Robert L. Petersen, Jr., Lake Zurich, Ill.

[73] Assignee: General Electric Company, Milwaukee, Wis.

[21] Appl. No.: 344,920

[22] Filed: Nov. 25, 1994

[51] Int. Cl.$^6$ .................................................. A61B 8/00
[52] U.S. Cl. .................. 128/660.01; 128/662.03
[58] Field of Search .................. 128/660.01, 660.07, 128/660.04–660.05, 661.01, 660.1, 662.03

[56] References Cited

U.S. PATENT DOCUMENTS

| | | | |
|---|---|---|---|
| 5,205,175 | 4/1993 | Garza et al. | 128/660.07 X |
| 5,207,225 | 5/1993 | Oaks et al. | 128/660.1 |
| 5,318,027 | 6/1994 | Fukui | 128/660.01 |
| 5,505,203 | 4/1996 | Deitrich et al. | 128/660.01 |

*Primary Examiner*—Francis Jaworski
*Attorney, Agent, or Firm*—Dennis M. Flaherty; John H. Pilarski

[57] ABSTRACT

An integral yoke/transducer connector has built-in probe switches for detecting when a transducer probe has been removed from its yoke. Based on the status of the probe switch and other feedback information, a system controller activates the out-of-holder probe if it has priority. In this manner, a probe can be automatically activated when it is lifted out of its yoke, thereby eliminating the need to trace a desired probe to its connector/port via the cable. Once a probe/port is auto-selected, it remains the only active probe/port until the probe is placed back in the yoke (or its transducer connector is disconnected from the port on the imaging unit). Placement of the probe in its corresponding yoke opens the probe switch which is built into the yoke/connector assembly. The imaging system can be provided with a plurality of interchangeable probe assemblies, each probe assembly consisting of a transducer probe, a coaxial cable, a transducer connector and a yoke, all four components being integrally attached to each other for installation and removal as an integral unit.

18 Claims, 5 Drawing Sheets

CLOSED: PROBE OFF HOOK
OPEN: PROBE ON HOOK 5,615,678

INTEGRAL AUTO-SELECTING YOKE/TRANSDUCER CONNECTOR FOR ULTRASOUND TRANSDUCER PROBE

FIELD OF THE INVENTION

This invention generally relates to ultrasound imaging of human tissue and blood. In particular, the invention relates to apparatus for connecting a plurality of transducer probes to an ultrasound imaging unit.

BACKGROUND OF THE INVENTION

Conventional ultrasound imaging systems have interchangeable transducer probes which are suitable for different applications. The transducer family may, for example, consist of four types of transducers: phased array, linear, convex and specialty (i.e., transducers designed for imaging specific body parts). Each transducer probe is coupled to a respective port of the ultrasound imaging system via a coaxial cable and a transducer connector. The transducer connectors are interchangeable in the sense that each connector can be plugged into any port. The console of the system is also conventionally provided with a set of yokes for holding the respective transducers when they are not being used. This set of yokes is typically placed on the side of the main unit or under the operator console of the main unit.

Each transducer probe is designed for a specific application. Depending on the desired application, the appropriate probe must be connected and activated before it can be used to scan the anatomy of interest. If four different transducer probes are plugged into the console, the user must select one of the four for the scanning operation.

Previous implementations of transducer selection require the user of the machine to select or activate one of the connector ports and thereby energize the transducer connected thereto by pressing a button or key. The specified probe then begins to image in response to that selection. The user must pick up the transducer from its holder either before or after selecting it via the button or key in order to apply it to the patient and actually begin scanning.

The foregoing implementation requires the user to know which transducer is connected to which port and then press the appropriate key corresponding to the picked-up transducer. When an operator wishes to use a particular probe on a multi-probe imaging unit, usually the operator must trace the transducer probe to its particular connector via the coaxial cable in order to determine which port the transducer connector is connected to. Thus, there is a need for a transducer activation scheme which allows the user to activate a desired transducer by the simple act of picking up the transducer.

SUMMARY OF THE INVENTION

The present invention is a probe assembly consisting of a transducer probe, a coaxial cable, a transducer connector and a yoke, all four components being integrally attached to each other for installation and removal as an integral unit. In particular, the probe assembly includes an integral yoke/transducer connector having built-in probe switches for detecting when a transducer probe has been removed from its yoke. Based on the status of the probe switch and other feedback information, a system controller activates the out-of-holder probe if it has priority. In this manner, a probe can be automatically activated when it is lifted out of its yoke, thereby eliminating the need to trace a desired probe to its connector/port via the cable.

Once a probe/port is auto-selected, it remains the only active probe/port until the probe is placed back in the yoke (or its transducer connector is disconnected from the port on the imaging unit). Placement of the probe in its corresponding yoke opens the probe switch which is built into the yoke. At that point, the same or another probe can be auto-selected by lifting it from its yoke. The probe switch in the integral yoke can be molded into the yoke or it can be designed to be separate and thus field-replaceable. Probes can be manually selected/activated via the operator interface in the event that the probe fails.

In accordance with the preferred embodiment of the invention, the ports are situated above the operator console on the front of the main unit. Situating the transducer connector ports at this height provides ease of connection and improved cable management (i.e., the cables are not as prone to be run over by or tangled in the wheels of a mobile imaging unit).

Another feature of the invention is that the individual yokes are designed such that the probes do not have to be placed into the yokes in any particular orientation. More specifically, the outer contour of the probe and the inner contour of the yoke are designed to be form-fitting. With this design, each transducer probe of different shape has its own customized yoke integrated with the transducer connector.

In accordance with this design, each probe can be placed into its yoke vertically but in no other particular orientation. When the probe is allowed to fall into place in the yoke, the contoured surfaces of the yoke cooperate with the contoured surfaces of the probe to guide the probe into its stored position. As the probe displaces downwardly relative to the yoke, the probe is rotated into an orientation that allows the probe to be snugly seated in the yoke. When seated snugly in the yoke, the probe will cause the probe switch to open, which indicates to the system that the probe is hooked in its yoke and can be deactivated.

DETAILED DESCRIPTION OF THE PREFERRED EMBODIMENT

Figure 1:
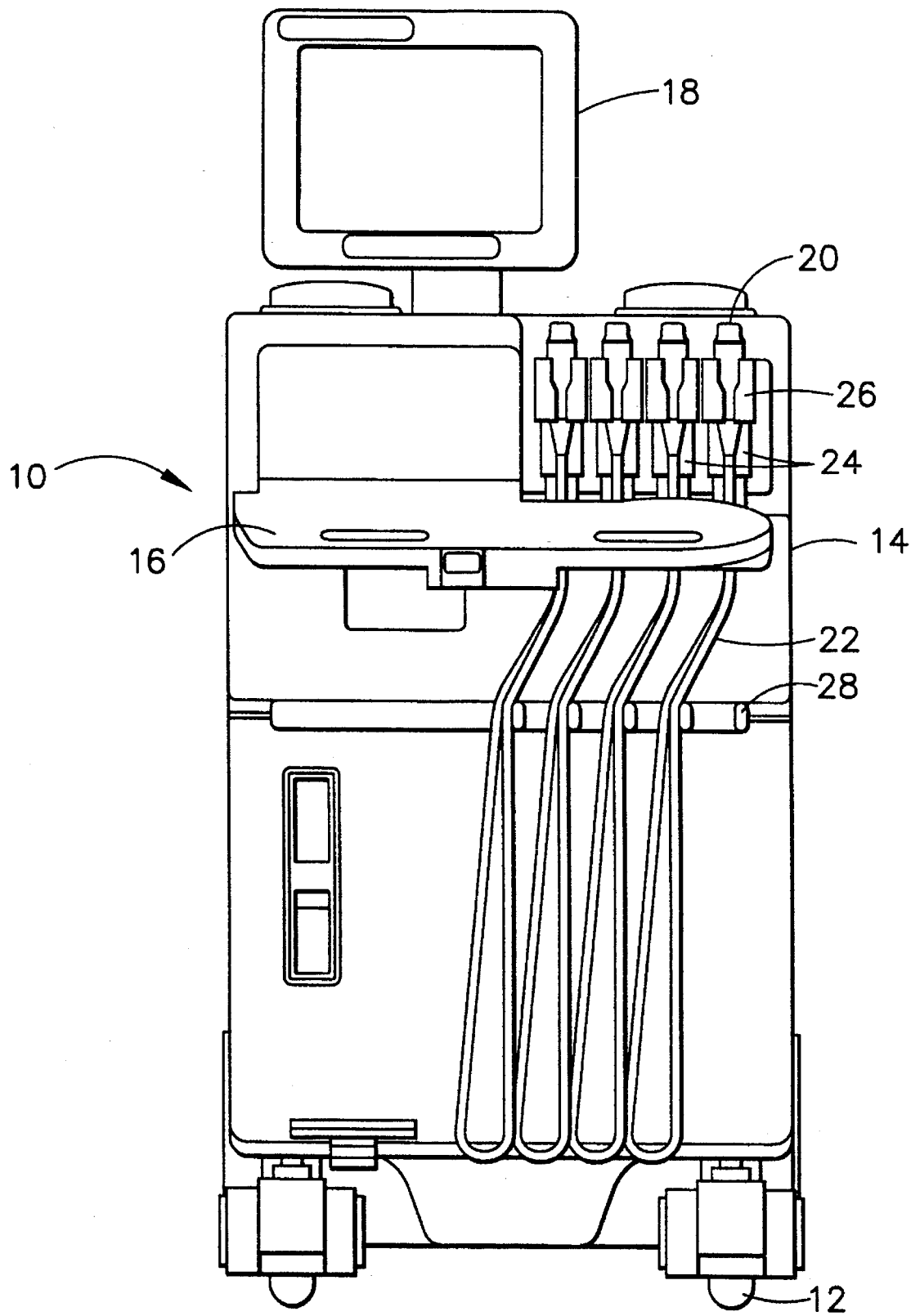
FIGS. 1 and 2 are front and side views respectively of an ultrasound imaging unit having a plurality of interchangeable probe assemblies, each probe assembly comprising an integral yoke/transducer connector in accordance with the present invention.
Figure 2:
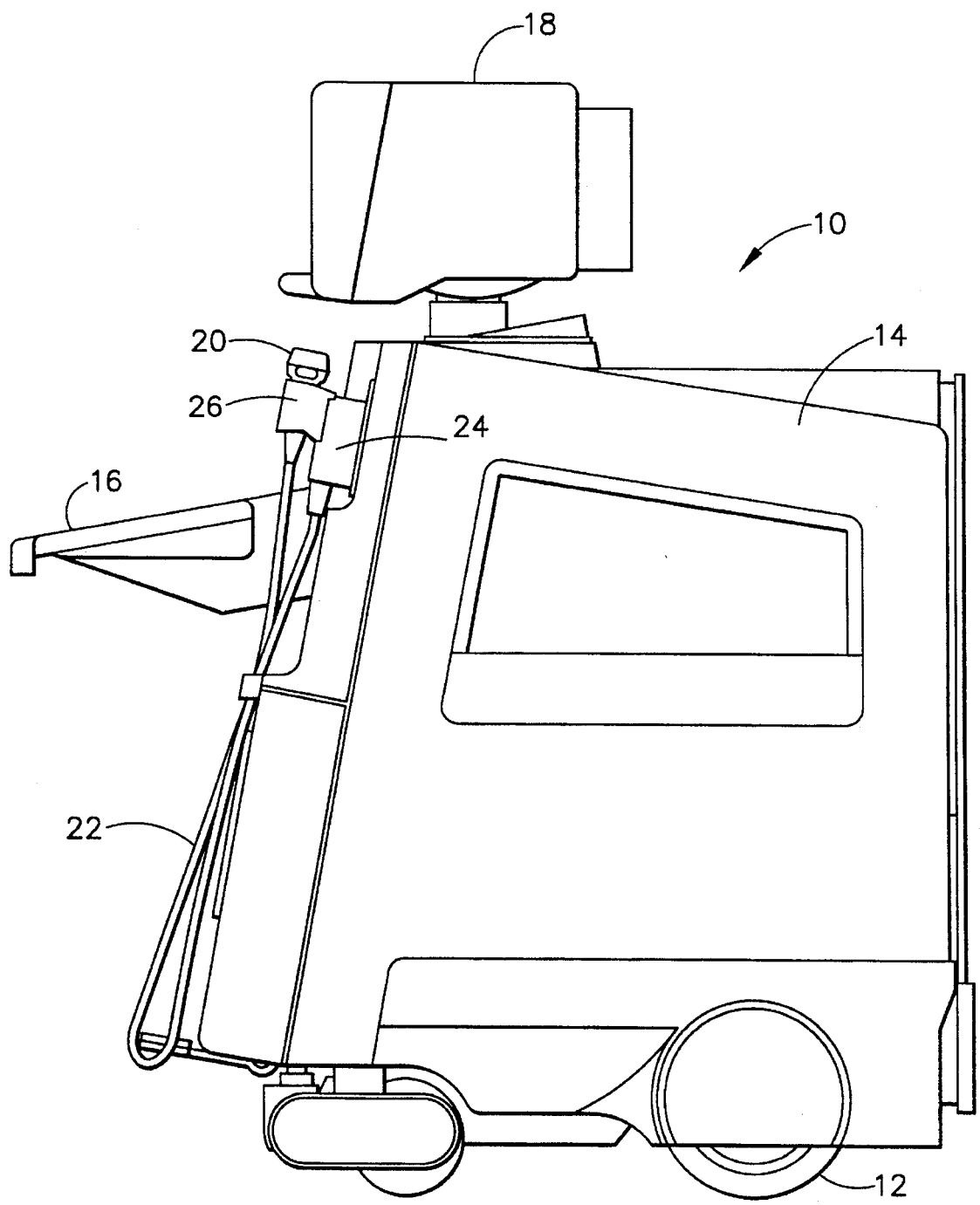

Referring to FIGS. 1 and 2, the ultrasound imaging unit in accordance with a preferred embodiment of the present invention comprises a mobile main unit 10 which is transportable on a plurality of wheels 12. The main unit includes a housing 14, an operator console 16 and a display monitor 18. The housing 14 has a plurality of ports (not shown) by means of which a plurality of transducer probes 20 can be coupled to the signal processing subsystems located inside housing 14. Typically each probe is designed to meet the requirements of a specific application. The transducers fall into four general categories: phased array, linear, convex and specialty (i.e., transducers designed for imaging specific body parts).

Each transducer probe is coupled to a respective port of the ultrasound imaging system via a coaxial cable 22 and a transducer connector 24. The transducer connectors are interchangeable in the sense that each connector can be plugged into any port.

A set of yokes 26 are provided for holding the respective transducers when they are not being used, as shown in FIGS. 1 and 2. The transducer probe, coaxial cable, connector and yoke form a transducer probe assembly. If the operator wishes to connect a different probe to the system, an entire probe assembly is removed and replaced by the new probe assembly.

When a transducer probe 20 is held in a yoke 26, the cable 22 is suspended with its lowest portion not touching the floor. If allowed to hang freely, the suspended cables could be tangled with each other. To prevent the cables from becoming tangled, a plurality of cable spacers 28 are arranged at spaced intervals at a height below the operator console. The spacing between midplanes of adjacent spacers 28 is approximately equal to the spacing between midplanes of the yokes 26. Further, the spacers 28 are offset relative to the mid-planes of the yokes, as best seen in FIG. 1. This offset makes it possible to loop each of the suspended cables 22 behind a corresponding spacer 28, thereby separating the cables from each other.

Figure 3:
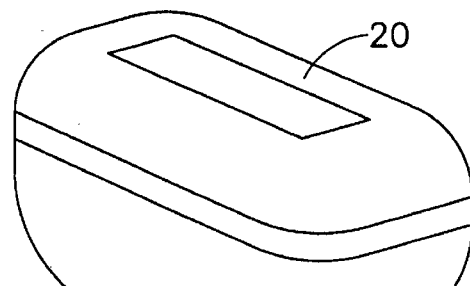
FIG. 3 is a concept drawing of an integral yoke/transducer connector in accordance with the preferred embodiment of the present invention.

The structure of the integral yoke/transducer connector in accordance with the preferred embodiment of the invention is shown in detail in FIG. 3. The transducer probe 20 has an array of transducer elements (not shown) which transmit ultrasound in a transmission mode and receive ultrasound echoes from the anatomy being examined in a reception mode. The signal electrodes of the transducer elements are electrically connected to one end of respective conductive wires (not shown) of the coaxial cable 22. The other end of the conductive wires of coaxial cable 22 are electrically connected to circuitry inside the connector box 30. The connector circuitry is in turn electrically connected to the port (not shown) in which it is plugged. That port is electrically connected to a transducer interface board (described in detail below with reference to FIG. 5).

Figure 6:
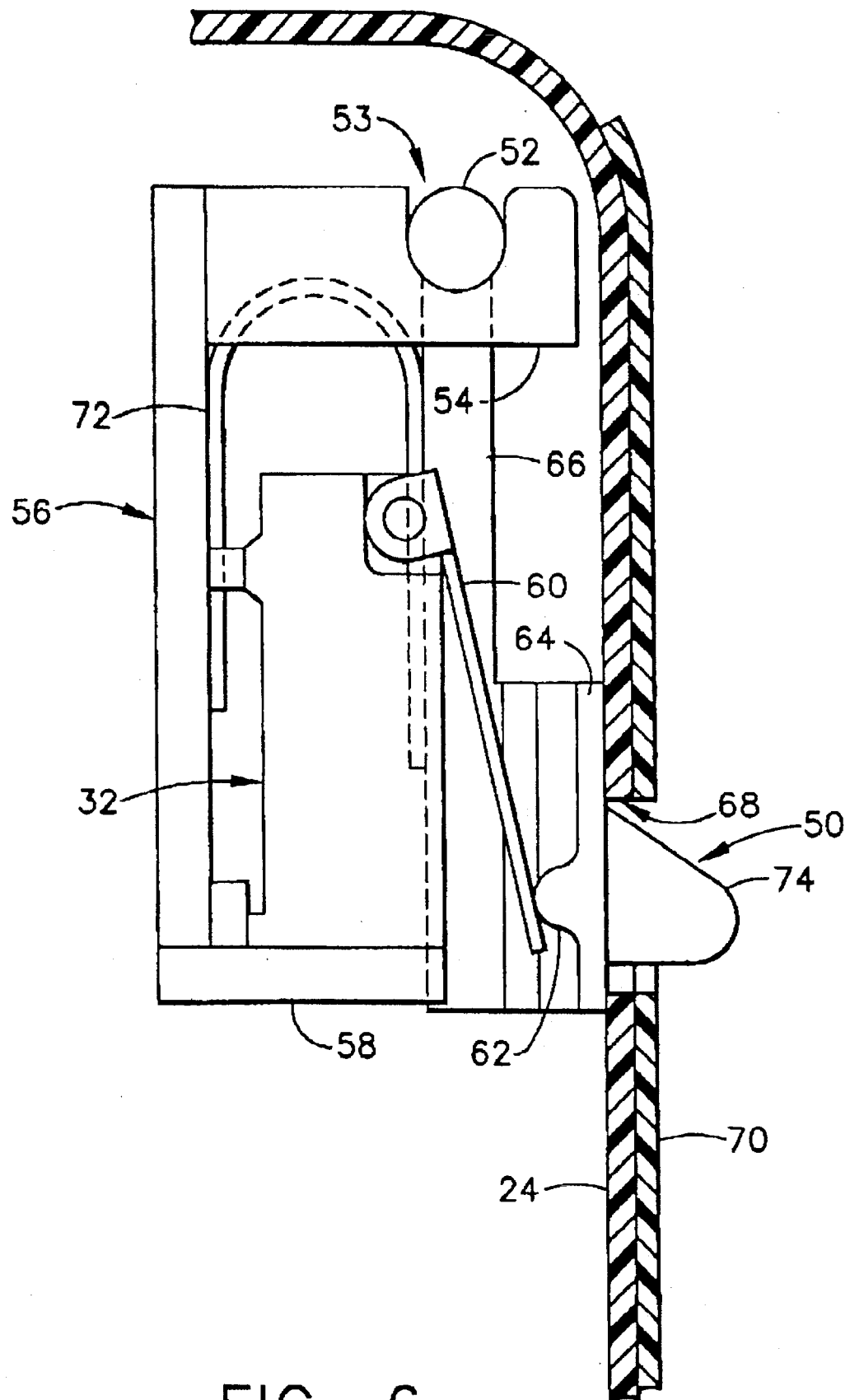
FIG. 6 is a schematic diagram showing the mechanical assembly for activating the probe switch when the probe is seated in the yoke in accordance with the preferred embodiment of the invention.

In accordance with the preferred embodiment shown in FIG. 6, a probe switch actuator 50 is incorporated in the integral yoke/transducer connector. This actuator has a pair of pivot pins 52 (only one of which is shown in FIG. 6) which are pivotably supported in respective slots 53 formed in a pair of arms 54 (only one of which appears in FIG. 6) which form part of a yoke assembly plate 56 securely mounted inside the connector box. Yoke assembly plate 56 also includes a support base 58, which supports the probe switch 32. The probe switch includes a contact arm 60 which is rotatable to open and close the probe switch 32, which is preferably a microswitch. The contact arm 60 is rotated to open the probe switch in response to a load exerted by a bearing pad 62 located at one end of the actuator sealing plate 64. The load is exerted by bearing pad 62 when the transducer probe is seated in the yoke space to cause the actuator 50 to pivot toward the yoke assembly plate 56. A generally U-shaped spring 72 has one arm which bears against and is supported by the yoke assembly plate 56 and another arm which bears against the pivot arm 66 of the actuator 50. Spring 72 urges actuator 50 to pivot away from the yoke assembly plate 56.

The actuator 50 has a contoured tongue 74 which is movable into and out of a position of interference with the transducer probe. Tongue 74 protrudes into the central space of the yoke via an opening 68 formed in the front wall of the connector box 24 and in the back wall 70 of the yoke 26. When the transducer probe is removed from the yoke, the tongue 74 of actuator 50 protrudes through opening 68 and into the central space of the yoke body in response to the urging of spring 72. When the transducer probe is returned to the yoke, the tongue 74 interferes with the seating of the transducer probe and is cammed out of the way by the probe when the force of the spring is counteracted.

When the transducer probe is returned to the yoke, it is dropped vertically downward into the yoke central space. As the probe displaces vertically downward, the probe housing will bear against the tongue 74, causing the actuator to pivot toward the yoke assembly plate 56. During this pivoting, the bearing pad 62 will displace along an arc for a distance sufficient to produce a rotation of contact arm 60 which causes a change in the ON/OFF state of the probe switch 32. A signal indicating this change of state is stored on the transducer interface board and transmitted to the master controller, as described in more detail below.

Figure 4:
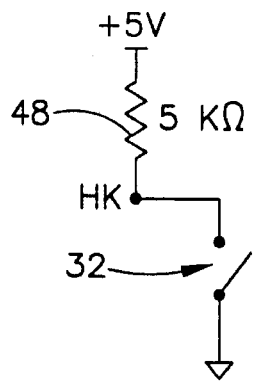
FIG. 4 is a circuit schematic for the probe present switch incorporated in the integral yoke/transducer connector depicted in FIG. 3.

Thus, the probe switch 32 functions as a means of telling the system when the probe 20 has been lifted out of the probe holder or yoke 26. The probe switch 32 supplies a simple "on" and "off" passive response (single pole, single throw). The switch is closed when the probe is off the yoke and open when the probe is on the yoke. The circuit schematic for the probe switch is shown in FIG. 4.

In accordance with the preferred embodiment, the actuator tongue 74 extends into the center space of the yoke 26 when the transducer probe is out of the yoke. The sealing plate 64 blocks entry of residual acoustic coupling gel into the interior of the connector box via opening 68. In accordance with a further aspect of the invention, the moving parts of the actuator assembly shown in FIG. 6, namely, pivot pins 52, contact arm 60 and spring 72, are all mounted at locations which are removed from the points of acoustic coupling gel entry, i.e., the portions of opening 68 not blocked by sealing plate 64 and tongue 74. Consequently, these moving parts are less susceptible to being rendered inoperable due to the accumulation over time of residual acoustic coupling gel.

Figure 5:
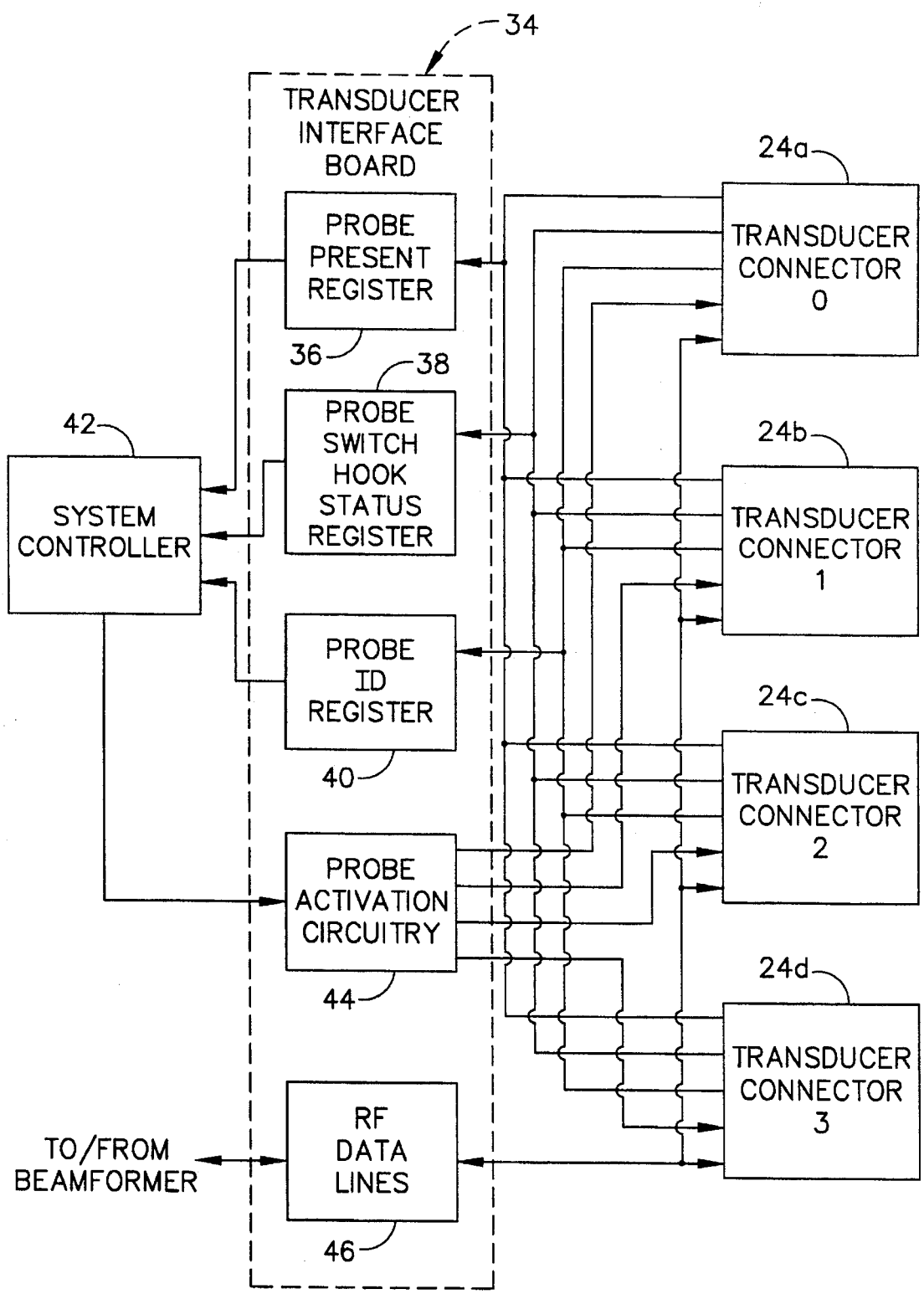
FIG. 5 is a block diagram of a transducer interface by which a plurality of transducer probes can be interfaced to an ultrasound imaging system.

The present invention is used in conjunction with transducer interface 34 shown in FIG. 5. Up to four transducer probes can be connected to the imaging system via transducer connectors 24a–2d. When any one of the transducer connectors is plugged into a corresponding port in the imaging system, a Probe Present signal is produced which is stored in the probe present register 36.

As described above, each connector 24a–2d has a probe switch 32 for indicating whether the corresponding probe is coupled to the corresponding yoke. The resulting probe switch hook status signal is input into the system via a pin labeled HK (see FIG. 4) on the transducer connector. This pin is pulled high by a 5 k$\Omega$ resistor 46 (see FIG. 4) on the transducer interface board 34. A transducer probe will either leave the pin floating, or ground the pin to form a signal indicating that the probe has been removed from its hook.

The resulting probe switch hook status signal is stored in the probe switch hook status register 38.

In addition, each transducer type has a unique 8-bit probe ID. There are 8 pins labeled PTY 0 to PTY 7 on the transducer connector. These pins are pulled high by 5 kΩ resistors on the transducer interface board 34. A transducer will either leave the pins floating, or ground them to form its unique probe ID. The probe ID signals are stored in probe ID register 40.

Depending on the contents of registers 36, 38 and 40, a system controller 42 outputs a Probe Select signal to the probe activation circuitry 44 on the transducer interface board 34. Probe activation circuitry 44 activates the selected transducer probe in response to that Probe Select signal.

The present invention can be used in conjunction with a transducer selection control program stored in system controller 42. The system controller periodically reads the contents of registers 36, 38 and 40 and processes the retrieved information in accordance with a stored algorithm to select a transducer for activation. The Probe Select signal sent to the probe activation circuitry 44 identifies the selected transducer. The selected transducer is activated by the probe activation circuitry 44 via the associated transducer connector. Radiofrequency data from the transducer element array is then multiplexed, under the control of the system controller, from the transducer connector to the beamforming circuitry (not shown) via the RF data lines 54 on the transducer interface board 34.

The foregoing preferred embodiment has been disclosed for the purpose of illustration. Variations and modifications will be readily apparent to those skilled in the art of ultrasound imaging systems. All such variations and modifications are intended to be encompassed by the claims set forth hereinafter.

We claim:

1. An integral probe assembly comprising:

an ultrasound transducer probe;

a transducer connector;

a coaxial cable having one end secured to said probe and another end secured to said transducer connector; and a yoke secured to said transducer connector, wherein said probe is configured to seat snugly within a center space of said yoke, and said yoke is supported by only said connector.

2. The integral probe assembly as defined in claim 1, further comprising a switch having a first state when said probe is snugly seated in said yoke and having a second state when said probe is removed from said yoke.

3. The integral probe assembly as defined in claim 2, wherein said transducer connector comprises connection circuitry located inside a connector housing, said switch being mounted in said connector housing and electrically connected to said connection circuitry.

4. The integral probe assembly as defined in claim 2, further comprising a switch actuator pivotably mounted in said connector housing, wherein said yoke has an opening through which said switch actuator protrudes into said center space.

5. The integral probe assembly as defined in claim 2, wherein said probe and said yoke have mutually form-fitting contours which cooperate to guide said probe into contact with said actuator during entry of said probe into said center space of said yoke from above, whereby said switch is changed from said second state to said first state.

6. An ultrasound imaging system comprising a main unit having a plurality of ports and a plurality of ultrasound probe assemblies, wherein each of said probe assemblies comprises:

an ultrasound transducer probe;

a transducer connector which can be plugged into any one of said plurality of ports;

a coaxial cable having one end secured to said probe and another end secured to said transducer connector;

a yoke secured to said transducer connector;

a switch having a first state when said probe is snugly seated in said yoke and having a second state when said probe is removed from said yoke; and a switch actuator pivotably mounted in said connector housing, wherein said yoke has an opening through which said switch actuator protrudes into said center space.

7. The ultrasound imaging system as defined in claim 6, wherein each of said transducer connectors comprises connection circuitry located inside a connector housing, said switch being mounted in said connector housing and electrically connected to said connection circuitry.

8. The ultrasound imaging system as defined in claim 7, further comprising an operator console, wherein said ports are arranged at a height above said operator console.

9. The ultrasound imaging system as defined in claim 8, further comprising means for supporting said main unit on a floor, wherein said cables do not reach the floor when said probes are seated in said respective yokes.

10. An ultrasound imaging system comprising a main unit having a plurality of ports and a plurality of ultrasound probe assemblies, wherein each of said probe assemblies comprises:

an ultrasound transducer probe;

a transducer connector which can be plugged into any one of said plurality of ports;

a coaxial cable having one end secured to said probe and another end secured to said transducer connector;

a yoke secured to said transducer connector; and a switch having a first state when said probe is snugly seated in said yoke and having a second state when said probe is removed from said yoke; and wherein said probe and said yoke of each of said probe assemblies have mutually form-fitting contours which cooperate to guide said probe into contact with said switch actuator during entry of said probe into said center space of said yoke from above, whereby said switch is changed from said second state to said first state.

11. An ultrasound imaging system comprising a main unit having a plurality of ports and a plurality of ultrasound probe assemblies, wherein each of said probe assemblies comprises:

an ultrasound transducer probe;

a transducer connector which can be plugged into any one of said plurality of ports;

a coaxial cable having one end secured to said probe and another end secured to said transducer connector;

a yoke secured to said transducer connector; and a switch having a first state when said probe is snugly seated in said yoke and having a second state when said probe is removed from said yoke; and wherein said probe is configured to seat snugly within a center space of said yoke, and said yoke is supported by only said connector.

12. A yoke/connector assembly for holding an ultrasound transducer probe, comprising:

a transducer connector housing having a front wall with an opening;

a yoke body having a central opening for receiving a probe and having a back wall with an opening, said yoke body being secured to said transducer connector housing such that said opening of said back wall of said yoke body is aligned with said opening in said front wall of said transducer connector housing;

an electrical switch having a pivotable arm which is pivotable between first and second angular positions, said switch being open when said arm is in one of said first and second angular positions and being closed when said arm is in the other of said first and second angular positions;

an actuator which is movable between first and second positions, said actuator comprising means for engaging said arm of said electrical switch such that said arm pivots from said first to said second angular position as said actuator moves from said first to said second position, and means for engaging a transducer probe as the transducer probe is lowered into said central opening such that said actuator moves from said first to said second position as the transducer probe is lowered from a first elevation to a second elevation, said probe engaging means projecting through said aligned openings; and a support plate comprising first means for supporting said switch and second means for supporting said actuator inside said transducer connector housing.

13. The yoke/connector assembly as defined in claim 12, wherein said actuator further comprises pivoting means and said support plate comprises means for pivotably supporting said pivoting means, whereby movement of said actuator between said first and second positions is performed by pivoting on said pivoting means.

14. The yoke/connector assembly as defined in claim 13, further comprising a spring which urges said actuator to pivot in a direction opposite to the direction said actuator pivots to cause said arm to pivot from said first angular position to said second angular position, wherein said support plate further comprises third means for supporting said spring.

15. The yoke/connector assembly as defined in claim 12, wherein said actuator further comprises means for blocking entry of acoustic coupling gel into said connector.

16. An ultrasound imaging system comprising a main unit having an operator console, a display monitor, means for supporting said main unit on a floor, a plurality of ports located at a height above said operator console, a plurality of spacers arranged at an elevation below said ports, each of said spacers being displaced relative to a vertical center plane passing through a respective port, and a plurality of interchangeable ultrasound probe assemblies, each of said probe assemblies comprising an ultrasound transducer probe, a transducer connector, a yoke secured to said transducer connector, and a coaxial cable having one end secured to said probe and another end secured to said transducer connector, wherein each of said transducer connectors can be plugged into any one of said plurality of ports and each of said cables does not reach the floor when said probes are seated in said respective yokes.

17. The ultrasound imaging system as defined in claim 16, wherein each of said probes is configured to seat snugly within a center space of a respective one of said yokes, and each of said yokes is supported by only a respective one of said connectors.

18. An ultrasound imaging system comprising a main unit having an operator console, a display monitor, means for supporting said main unit on a floor, a plurality of ports located at a height above said operator console, and a plurality of interchangeable ultrasound probe assemblies, each of said probe assemblies comprising an ultrasound transducer probe, a transducer connector, a yoke secured to said transducer connector, and a coaxial cable having one end secured to said probe and another end secured to said transducer connector, wherein each of said transducer connectors can be plugged into any one of said plurality of ports and each of said cables does not reach the floor when said probes are seated in said respective yokes, wherein said probe and said yoke have mutually form-fitting contours which cooperate to guide said probe into a position whereat said probe is snugly seated in said yoke.

* * * * *